US00PP25477P3

(12) United States Plant Patent
Kardos

(10) Patent No.: US PP25,477 P3
(45) Date of Patent: Apr. 28, 2015

(54) ***LAGERSTROEMIA* PLANT NAMED 'PIILAG B2'**

(50) Latin Name: *Lagerstroemia indica×L. fauriei*
Varietal Denomination: PIILAG B2

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 13/815,402

(22) Filed: Feb. 28, 2013

(65) Prior Publication Data

US 2014/0245505 P1 Aug. 28, 2014

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

U.S. PATENT DOCUMENTS

| | | | |
|---|---|---|---|
| PP10,319 | P | 4/1998 | Whitcomb |
| PP16,917 | P2 | 8/2006 | Dirr |
| PP17,411 | P2 | 2/2007 | Dirr |
| PP21,540 | P2 | 11/2010 | Knight |
| PP22,161 | P2 | 9/2011 | Dirr |
| PP23,071 | P3 | 9/2012 | Dirr |
| PP23,168 | P3 | 11/2012 | Griffith |
| PP23,178 | P3 | 11/2012 | Dirr |
| PP23,518 | P3 | 4/2013 | Kardos |
| 2013/0125275 | P1 | 5/2013 | Kardos |
| 2013/0125276 | P1 | 5/2013 | Kardos |

OTHER PUBLICATIONS

First Editions Collection webpage, (downloaded Mar. 6, 2013, available on Internet in Jan. 2013), "*Lagerstroemia* 'PIILAG-IV'", http://www_._firsteditionsplants_._com/collection, 1 page.
First Editions Collection webpage, (downloaded Mar. 6, 2013, available on Internet in Jan. 2013), "*Lagerstroemia* 'PIILAG-V'", http://www_._firsteditionsplants_._com/collection, 1 page.
American Nurseryman Catalog, "2013_AN_Woody Plants," Dec. 2012, p. W5.

*Primary Examiner* — Kent L Bell
(74) *Attorney, Agent, or Firm* — Lathrop & Gage LLP

(57) ABSTRACT

A new and distinct cultivar of *Lagerstroemia* plant named 'PIILAG B2', characterized by its compact, rounded intermediate growth habit, reddish purple new growth, cupped, lustrous dark green foliage in summer, clear pink flowers, and resistance to powdery mildew and *Cercospora* leaf spot.

2 Drawing Sheets

Genus and species of plant claimed: *Lagerstroemia indica×L. fauriei.*

Variety denomination: 'PIILAG B2'.

BACKGROUND OF THE INVENTION

The present invention relates to a new and distinct cultivar of *Lagerstroemia* plant, botanically known as *Lagerstroemia indica×L. fauriei*, commonly known as crapemyrtle, and hereinafter referred to by the cultivar name 'PIILAG B2'. 'PIILAG B2' is grown primarily as an ornamental for landscape use and for use as a potted plant.

'PIILAG B2' originated from open-pollinated seed of *Lagerstroemia indica×L. fauriei* 'Gamad VI' (U.S. Plant Pat. No. 22,161) growing in Watkinsville, Ga. The cultivar 'PIILAG B2' originated in 2008 and was selected in a cultivated environment in Watkinsville, Ga. from the progeny of this open-pollination by continued evaluation for growth habit and foliage and flower characteristics.

Asexual reproduction of 'PIILAG B2' by stem cuttings in Watkinsville, Ga. since 2009 has shown that all the unique features of this new *Lagerstroemia*, as herein described, are stable and reproduced true-to-type through successive generations of such asexual propagation.

SUMMARY OF THE INVENTION

Plants of the new cultivar 'PIILAG B2' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG B2'. These characteristics in combination distinguish 'PIILAG B2' as a new and distinct cultivar: 1. Compact, rounded intermediate growth habit; 2. Reddish purple new growth; 3. Cupped, lustrous dark green foliage in summer; 4. Clear pink flowers; 5. Resistance to powdery mildew and *Cercospora* leaf spot.

Plants of 'PIILAG B2' differ from plants of the parent, 'Gamad VI', primarily in growth habit, foliage, flower color, and time of flowering. Plants of 'Gamad VI' have a compact, mounded growth habit, flattened foliage, and produce deep red and purple flowers in early summer, whereas plants of 'PIILAG B2' have an overall larger, compact, rounded intermediate growth habit, cupped foliage, and clear pink flowers in mid-summer.

Plants of 'PIILAG B2' can be compared to the cultivar 'Gamad V' (U.S. Plant Pat. No. 17,411), but differ in overall size, foliage color, and flower color. Plants of 'PIILAG B2' have a compact, rounded intermediate growth habit, foliage that emerges reddish purple, and clear pink flowers, whereas plants of 'Gamad V' have an overall smaller, dwarf growth habit, medium green new growth, and lighter pink flowers.

BRIEF DESCRIPTION OF THE DRAWINGS

The accompanying color photographs illustrate the flower and foliage characteristics and the overall appearance of 'PIILAG B2', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
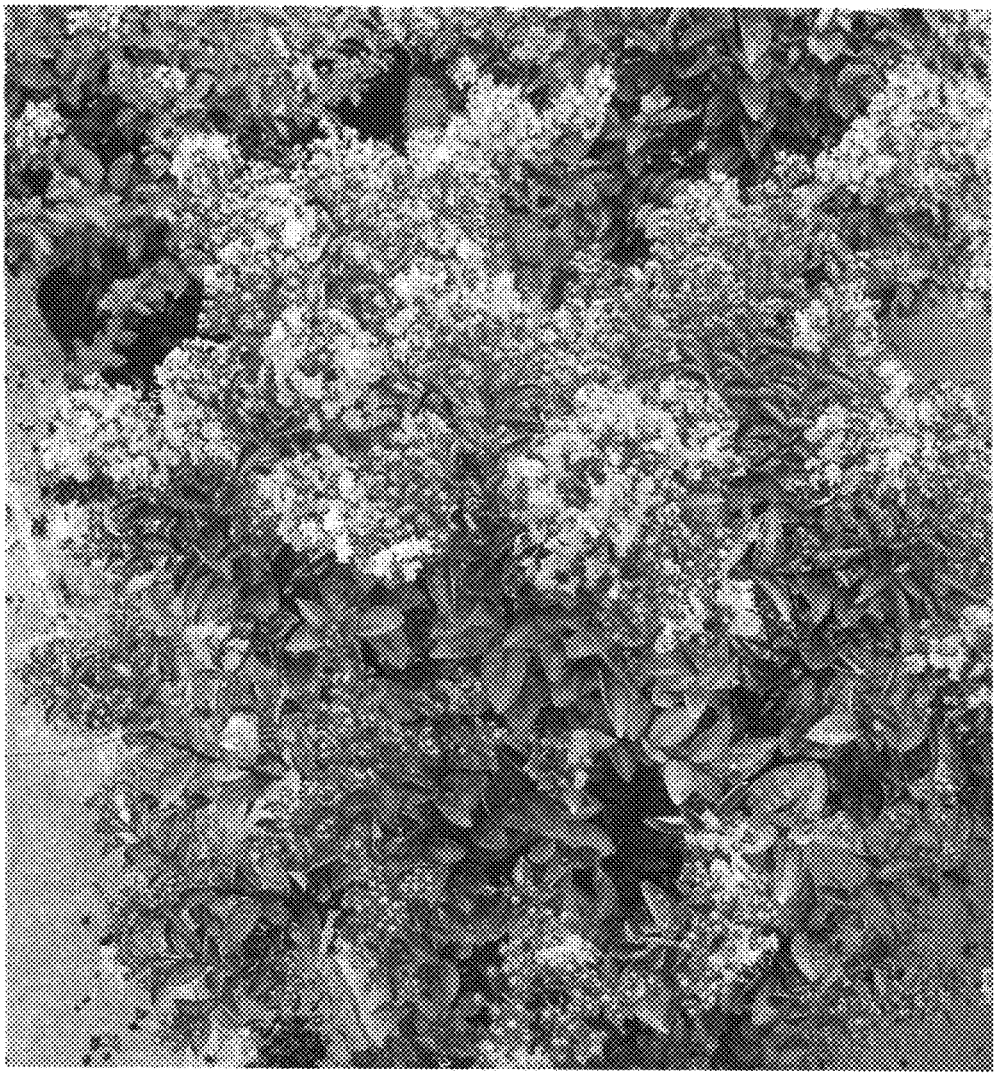
FIG. 1 illustrates the overall appearance of a mature plant of 'PIILAG B2' in a container.
Figure 2:
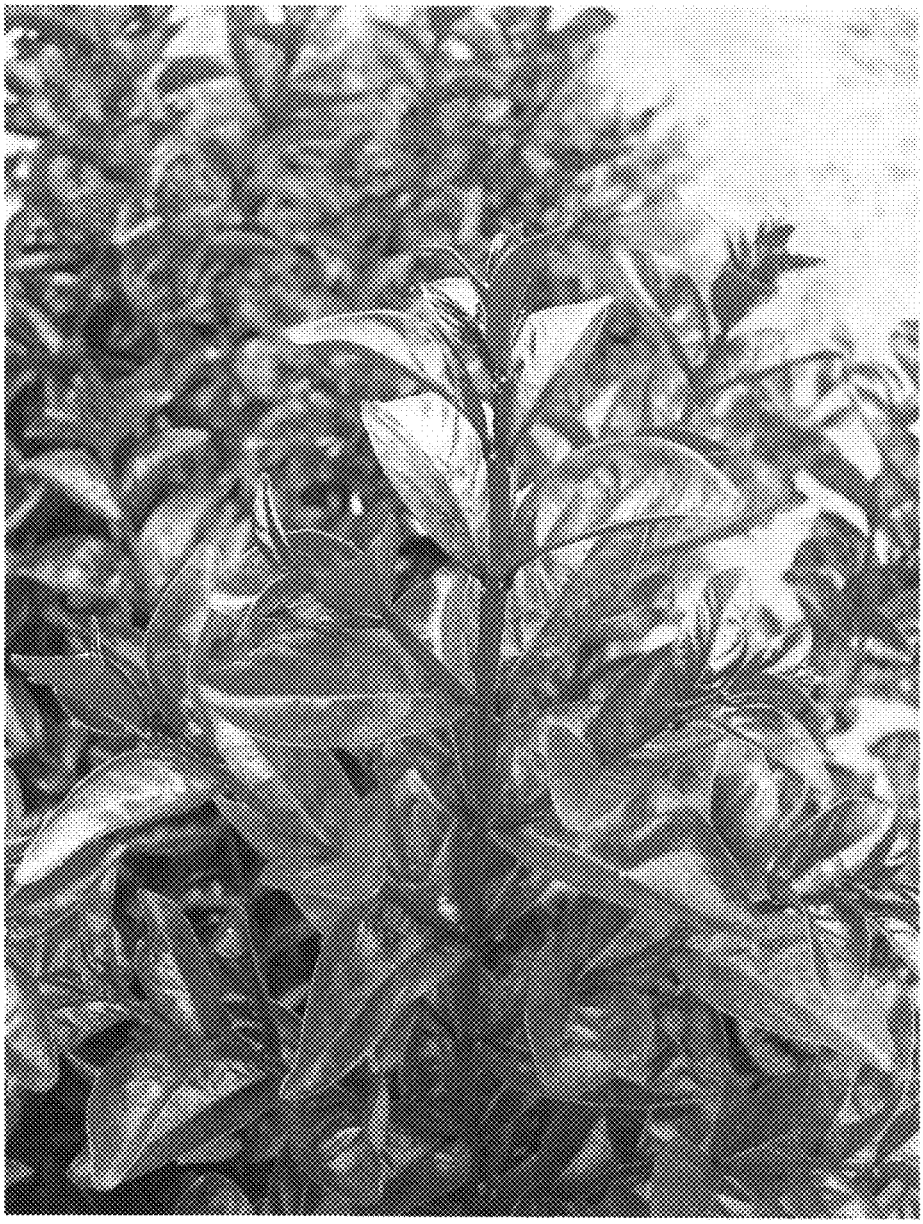
FIG. 2 illustrates a close-up view of the new growth of 'PIILAG B2'.

In the following description, color references are made to The Royal Horticultural Society Colour Chart, 2007 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG B2'.

Parentage:

*Female, or seed, parent.*—*Lagerstroemia* 'Gamad VI' (U.S. Plant Pat. No. 22,161).

*Male, or pollen parent.*—Unknown (open-pollinated).

Propagation: Terminal cuttings.

*Time to initiate roots, summer.*—About 21 days at 32° C.

Plant description: Flowering shrub: compact, rounded intermediate growth habit. Freely branching; lateral branches abundant without pruning, resulting in fine-textured, dense habit.

*Root description.*—Numerous, fine, fibrous and well-branched.

*Plant size.*—The original plant, now about five-years-old in the ground, is about 137 cm high from the soil level to the top of the inflorescences and about 137 cm wide. First year stems have a diameter of about 2.5 mm. First year stems have length of 30.48 cm to 45.75 cm. Shape: squarish. Second year and older stems have a diameter of about 5 mm or more. Second year stems have length of 60.96 cm to 91.44 cm. Shape: round.

*Trunk diameter.*—3.2 cm at the soil line. Color: N199B.

*Internode length.*—About 1.9 cm.

*Strength.*—Flexible when young, easily broken once mature.

*First year stem color* (*young*).—179A. Color (woody): 200D.

*Second year and older stem color.*—N199B.

*Bark.*—Exfoliates in strips beginning on second or third year stems.

Vegetative buds: Sub-opposite to alternate in arrangement, imbricate, conical, with no pubescence.

*Color.*—178C.

*Size.*—About 2.5 mm in length and 1 mm in width.

Foliage description:

*Arrangement.*—Sub-opposite to alternate, simple.

*Length.*—About 4.6 cm.

*Width.*—About 2.7 cm.

*Shape.*—Elliptical.

*Apex.*—Acuminate.

*Base.*—Cuneate.

*Margin.*—Entire.

*Texture* (*upper and lower surfaces*).—Glabrous and glossy.

*Venation pattern.*—Pinnate.

*Venation color of emerging foliage* (*upper and lower surfaces*).—179A.

*Venation color of fully expanded foliage* (*upper and lower surfaces*).—144A.

*Color in developing foliage* (*upper and lower surfaces*) .—179A.

*Color in fully expanded foliage* (*upper surface*).—147A.

*Color in fully expanded foliage* (*lower surface*).—146C.

*Petiole length.*—About 2 mm.

*Petiole diameter.*—About 1 mm.

*Petiole color* (*upper and lower surfaces*).—144A.

*Pubescence.*—None.

Flower description: Flowers are produced from about June to September in Watkinsville, Ga. An inflorescence is showy for about two weeks, and individual flowers last about one day and are self-cleaning. Flowers are lightly fragrant.

*Inflorescence type.*—Panicle. Panicle contains between 20 to 150 buds or flowers.

*Inflorescence length.*—About 10.2 cm.

*Inflorescence width.*—About 10 cm.

*Peduncle.*—About 8.5 cm in length, about 2 mm in diameter, color is 179A, and no pubescence.

*Individual flowers.*—About 2.2 cm in height and 2.9 cm in diameter.

*Flower buds.*—Length: about 7 mm; Diameter: about 7 mm; Color: 186B. Unopened flower buds are globose with six distinct lines of dehiscence where they split to reveal the flower.

*Sepals.*—Arrangement/quantity: single whorl of six fused sepals. Length: about 9 mm. Width: about 4 mm. Shape: elliptical. Apex: acute. Margin: entire. Texture, upper and lower surfaces: smooth, glabrous. Color: when opending, upper surface: 157A. When opening, lower surface: 146A. Fully opened, upper surface: 157A. Fully opened lower surface: 146A slightly tinged with 63A.

*Pedicels.*—About 7 mm in length, 1 mm in diameter, 179A in color, and no pubescence.

*Calyx.*—About 7 mm in length, about 1 cm in diameter, 186B on both surfaces, and no pubescence.

Petals:

*Arrangement/appearance.*—Usually 6 or 7 per flower.

*Petal length.*—About 1.5 cm.

*Petal width.*—About 1.2 cm.

*Petal shape.*—Fan-shaped.

*Petal apex.*—Ruffled, rounded.

*Petal base.*—Sagittate.

*Petal margin.*—Undulate.

*Petal texture* (*upper and lower surfaces*).—Glabrous.

*Petal color.*—Upper and lower surfaces are N66C.

Stamens:

*Quantity/arrangement.*—About 25 to 30 short stamens clustered in the center, about 7 mm long, filament color is 62D, and anther color is 2B. The short stamens are surrounded by 6 longer stamens, about 1.3 cm long, filament color is 65A, and anther color is 2B. The stamens are not pubescent.

*Pollen*.—Produced in moderate quantities and is 6A in color on the short and long stamens.

Pistils:

*Quantity*.—One superior pistil per flower.

*Pubescence*.—None.

*Pistil length*.—About 1.7 cm in length.

*Stigma shape*.—Round, about 1 mm in diameter.

*Stigma color*.—144C.

*Style color*.—181D and about 1.4 cm in length.

*Ovary color*.—8C and about 2 mm in diameter.

Fruit:

*Type/appearance*.—Six-valued, dehiscent, broad ellipsoidal capsule.

*Length*.—About 8 mm.

*Diameter*.—About 7 mm.

*Immature color*.—144A.

*Mature color*.—200C. Each capsule contains many seeds that are about 5 mm long, 3 mm wide, and 200C in color.

Plant hardiness:

*Plant hardiness*.—USDA Plant Hardiness Zone Map (2012): Zone 6 to 9.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG B2', as illustrated and described herein.

* * * * *